United States Patent
Schmidt et al.

(10) Patent No.: US 8,030,086 B2
(45) Date of Patent: Oct. 4, 2011

(54) METHOD, PARTICLE SENSOR AND PARTICLE SENSOR SYSTEM FOR MEASURING PARTICLES

(75) Inventors: Ralf Schmidt, Gerlingen (DE); Henrik Schittenhelm, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 955 days.

(21) Appl. No.: 11/629,740

(22) PCT Filed: Apr. 26, 2005

(86) PCT No.: PCT/EP2005/051848
§ 371 (c)(1),
(2), (4) Date: Jun. 8, 2007

(87) PCT Pub. No.: WO2005/124326
PCT Pub. Date: Dec. 29, 2005

(65) Prior Publication Data
US 2007/0264158 A1 Nov. 15, 2007

(30) Foreign Application Priority Data
Jun. 18, 2004 (DE) .......................... 10 2004 029 523

(51) Int. Cl.
*G01N 21/72* (2006.01)
(52) U.S. Cl. ..................................... 436/155
(58) Field of Classification Search .................. 436/155
See application file for complete search history.

(56) References Cited

U.S. PATENT DOCUMENTS

| 4,307,061 A | 12/1981 | Sarholz | |
|---|---|---|---|
| 5,123,243 A * | 6/1992 | Baddour | 60/274 |
| 6,517,786 B1 * | 2/2003 | Best et al. | 422/186.04 |

FOREIGN PATENT DOCUMENTS

| DE | 33 04 548 | 8/1984 |
| DE | 101 33 384 | 1/2003 |
| EP | 0 525 566 | 2/1993 |
| JP | 60 123757 | 1/1985 |

* cited by examiner

*Primary Examiner* — Vickie Kim
*Assistant Examiner* — Dwan A Gerido
(74) *Attorney, Agent, or Firm* — Kenyon & Kenyon LLP

(57) ABSTRACT

A method and a particle sensor for measuring particles, especially soot particles, in which the particles to be detected accumulate in a measuring region of the particle sensor. The particles located in the gas stream or the particles already accumulated in the measuring region are burned by a combustion device, the combustion being controlled via a control signal from a control unit, which is electrically connected to a measuring device, in such a way that the quantity of the particles adhering in the measuring region remains constant. The physical variable of the combustion device, which leads to the controlled combustion of the particles, is drawn upon as the signal amplitude of the particle sensor.

9 Claims, 3 Drawing Sheets

METHOD, PARTICLE SENSOR AND PARTICLE SENSOR SYSTEM FOR MEASURING PARTICLES

FIELD OF THE INVENTION

The exemplary embodiment(s) and/or exemplary method(s) of the present invention relates to a method, a particle sensor and a particle sensor system for measuring particles, especially soot particles.

BACKGROUND INFORMATION

In order to measure particles, such as soot particles, in the exhaust gas of internal combustion engines, a particle sensor having a device for the detection of soot particles may be mounted in the exhaust pipe.

A sensor is discussed in German patent document no. DE 101 33 384 A1 which is made up of two base (substrate) elements, the base elements having interdigital electrodes and an integrated heater, and being laminated to each other. The interdigital electrodes are used for measuring soot particles, the measurement being based on a resistive measuring principle: An accumulation of particles on the electrode structure leads to a conductivity change or impedance change of the area between the combs of the electrode. From the change, the accumulation, or rather, the accumulation rate of the particles may be derived. After a certain accumulation quantity, the sensor has to be regenerated, that is, the sensor has to be freed of accumulated particles. To do this, the integrated heater heats the sensor encumbered with soot, so that the accumulated soot is completely burned off. Then the sensor is again in the original state, and a renewed accumulation and measurement of particles are thereby made possible.

One advantage of this procedure comes about because, during the combustion, no new accumulation of particles is possible. Even after the regeneration, soot cannot immediately be accumulated again, for, because of thermal inertia, the sensor requires a certain time for the thermalization of the sensor element by the exhaust gas. Since, during the regeneration phase and the subsequent cooling phase of the sensor, no soot is able to be accumulated, during these phases the sensor is insensitive with respect to a possibly present soot concentration.

SUMMARY OF THE INVENTION

The exemplary method according to the present invention for measuring particles in a gas stream, especially soot particles, has the advantage that a signal amplitude is generated at least approximately continuously. Insensitive phases with respect to particle concentration during the detection of particles do not occur any more.

Moreover, a sensor for measuring particles as well as advantageous refinements related to it is given in the claims.

The sensor according to the present Application demonstrates a very compact construction, so that its use is made possible not only in the exhaust branch of a motor vehicle but in all those places where monitoring soot concentration is necessary or desirable in a space saving way.

DETAILED DESCRIPTION

Figure 1:
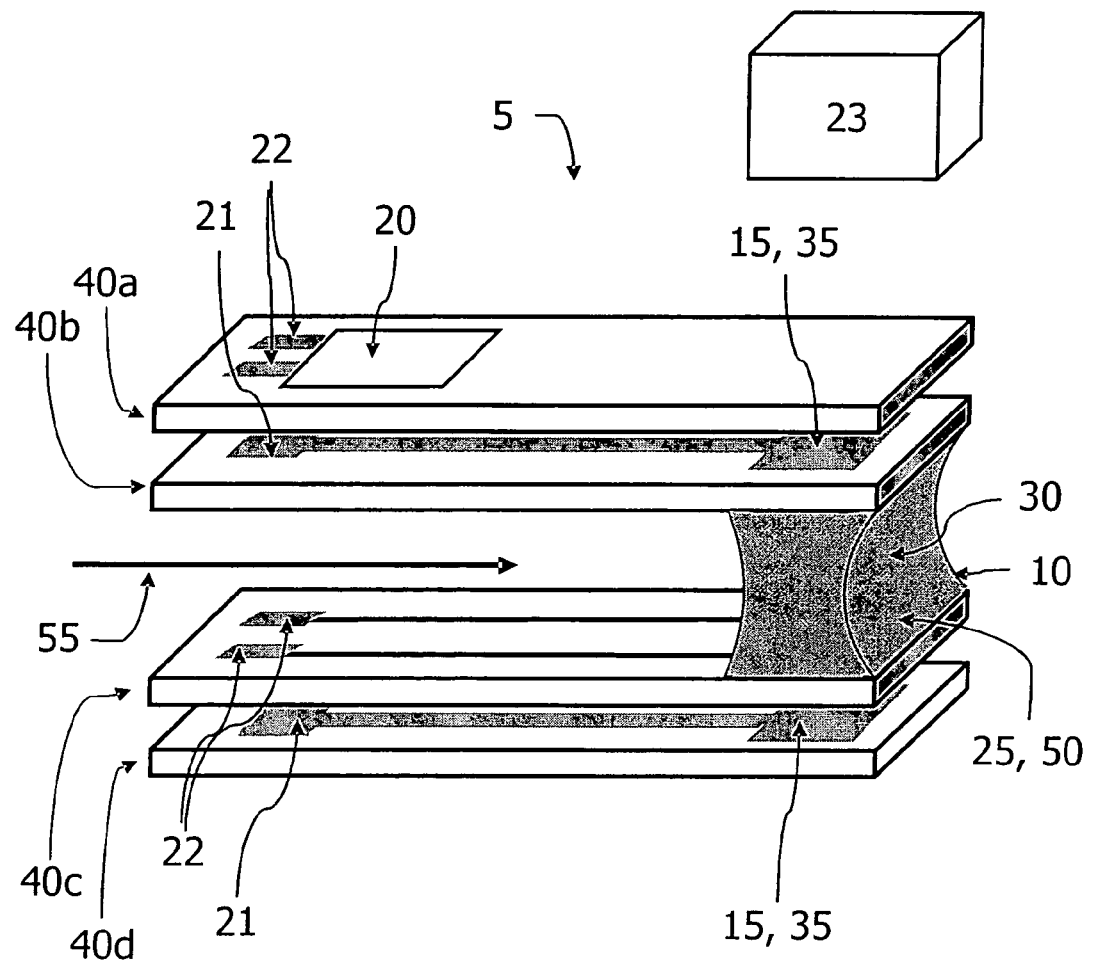
FIG. 1 shows a first exemplary embodiment of a particle sensor for measuring particles, in a schematic representation.
Figure 2:
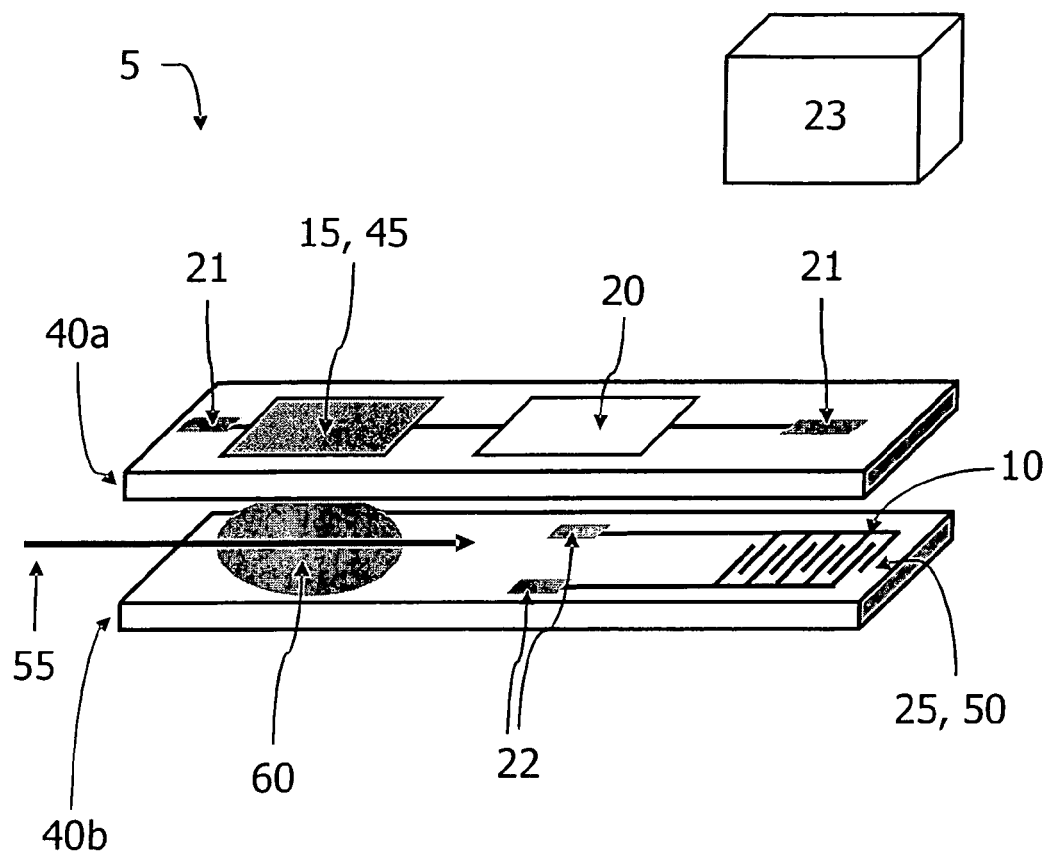
FIG. 2 shows a second exemplary embodiment of a particle sensor for measuring particles, also in a schematic representation.
Figure 3:
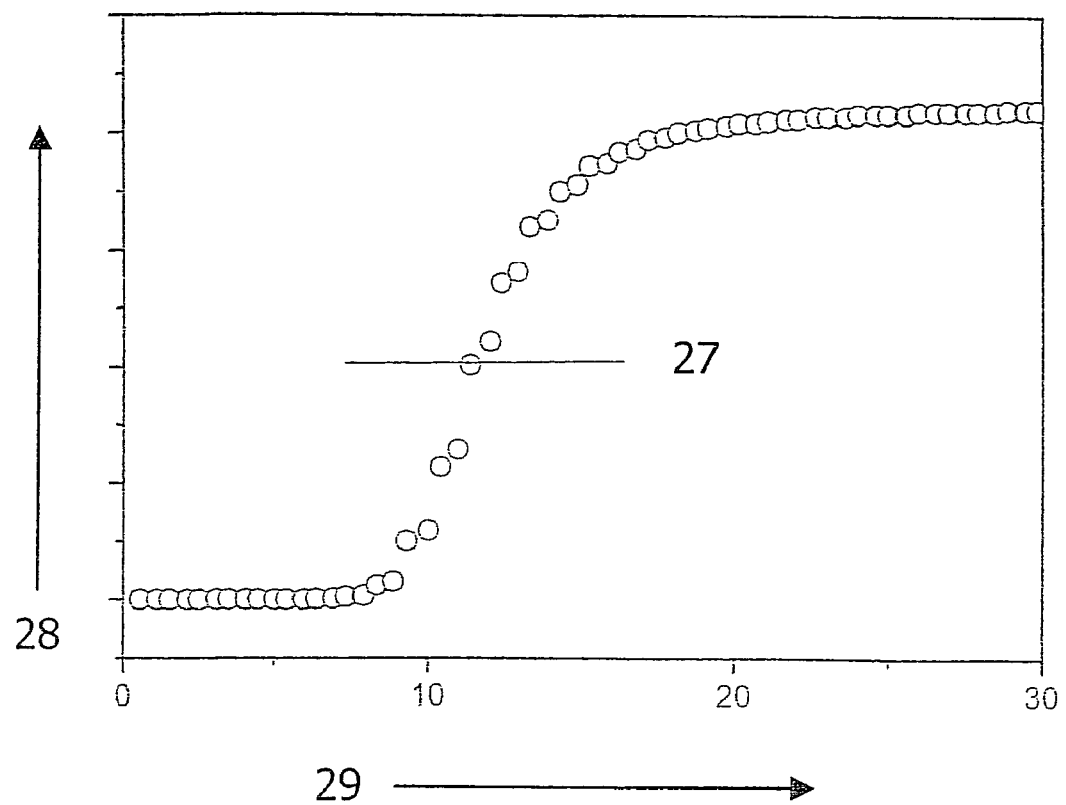
FIG. 3 shows a curve of the measured value of the measuring device plotted against the accumulation time, in the range of the percolation threshold.

FIGS. 1 and 2 show a sensor for the detection of particles in a gas stream, which is used for installation in an exhaust branch of a motor vehicle, and may be situated downstream of a soot filter of a motor vehicle having a Diesel internal combustion engine. Alternatively, the sensor may also be situated upstream from the soot filter, in order to determine the soot input into the filter.

In a first exemplary embodiment as in FIG. 1, particulate sensor 5 has four base elements 40a, 40b, 40c, 40d. Base elements 40a, 40b, 40c, 40d are situated parallel to one another and congruent one above the other, between the two middle ones, 40b, 40c of the four base elements 40a, 40b, 40c, 40d, a greater clearance is provided as compared to the clearance between the two outer ones 40a, 40b and 40c, 40d of the four base elements 40a, 40b, 40c, 40d. Thus, base elements 40a and 40b, as well as 40c and 40d are laminated to each other, whereas between base elements 40b and 40c a gap is provided for gas stream 55. In this description, the uppermost base element is designated as the first, 40a, and the lowest as the fourth, 40d. Base elements 40a, 40b, 40c, 40d are made up of a highly insulated material, for instance a ceramic, such as aluminum oxide (laminated $Al_2O_3$ foils).

A combustion device 15 is implemented in the first exemplary embodiment by a discharge device having two discharge electrodes 35. The two discharge electrodes 35 are mounted separately on two of the four base elements 40a, 40b, 40c, 40d, for instance, on the upper side of the second, 40b, and the fourth, 40d, base element, as shown in FIG. 1. The upper side of second base element 40b faces first base element 40a, and, likewise, the upper side of fourth base element 40d faces third base element 40c. The third, 40c, of the four base elements 40a, 40b, 40c, 40d is situated between the two discharge electrodes 35, and is used as a dielectric of discharge electrodes 35. Naturally, this applies also if discharge electrodes 35 are situated on the lower side of the respective base element 40b, 40d. Discharge electrodes 35 may have voltages applied to them via contacting areas 21, whereby a dielectrically impeded discharge (DBE) is ignited. The result of this is a cold DBE plasma 30.

A measuring device 25 is provided on the third, 40c, of the four base elements 40a, 40b, 40c, 40d, and in such a way that measuring device 25 is situated at the same time between the two discharge electrodes 35. Measuring device 25 is typically situated on the upper side of third base element 40c, and is therefore freely accessible to the soot coming from the exhaust gas. Advantageously, measuring device 25 is an interdigital comb electrode structure. In FIG. 1, interdigital comb electrodes 50 are covered by DBE plasma 30, and are therefore not shown explicitly, but they are sketched in FIG. 2. The range of measuring device 25 defines measuring range 10, on which the particles to be detected accumulate.

A control unit 20 for controlling the partial regeneration by combustion device 15 is provided on one of the four base elements 40a, 40b, 40c, 40d. However, if necessary, it may also be situated outside the four base elements 40a, 40b, 40c, 40d in a control unit 23. In any case, control unit 20 is electrically connected via contact areas 21, 22 both to combustion device 15 and to measuring device 25. The electrical connection via contact areas 21, 22 is not shown in FIGS. 1 and 2, for reasons of clarity.

For the continuous or semicontinuous measurement of particles, especially soot particles, particle sensor 5 is positioned in a gas stream 55 having the particles to be detected, so that the particles accumulate in the measuring region 10. The particles accumulated in measuring region 10 are measured by measuring device 25, which may be interdigital comb electrodes 50. The accumulation of particles leads to a conductivity change or impedance change between comb electrodes 50.

After the measurement of the accumulated particles by interdigital comb electrodes 50, the sensor is totally regenerated according to known methods by combustion device 15, that is, the sensor is completely liberated from all particles adhering to the sensor. In contrast thereto it is provided to carry out a partial regeneration of the sensor instead of a total regeneration, in such a way that equilibrium is reached between the soot removed by the partial regeneration, that is, by a combustion, and the newly accumulated soot. This makes it possible, in a continual or nearly continual manner, to determine the soot concentration present and the accumulation rate of the particles. One may then do without a total regeneration. We specifically wish to point out that, in this document, by "combustion" we mean an oxidation process, that is, even a process without a considerable temperature increase, such as an oxidation process by a so-called "cold plasma", is counted as such.

For a controlled partial regeneration, combustion device 15 is constantly supplied with a control signal from control unit 20. The control signal may be a current signal or a voltage signal. Thereby, the performance (efficiency) of the combustion adapts continuously to the current situation, so that the removal rate of the particles is equal to the accumulation rate in terms of the absolute value. In order to maintain the desired equilibrium, at large particle flows, measuring region 10 of particle sensor 5 is more strongly partially regenerated than at relatively small particle flows.

In FIG. 1, combustion device 15 is a discharge device having discharge electrodes 35. The combustion of the accumulated particles is carried out in this case using a cold DBE plasma 30. The advantage of using a cold DBE plasma 30 is that no thermal heating occurs on particle sensor 5.

Finally, the signal amplitude of particle sensor 5 is ascertained. Besides the control signal from control unit 20, the physical variable of combustion device 15, which leads to the controlled partial regeneration of measuring region 10, and the signal amplitude of particle sensor 5 may be drawn upon. In the case of the discharge device having discharge electrodes 35 as the combustion device 15, the performance of DBE plasma 30 is a suitable variable.

In order to assure as high as possible a sensitivity of the measurement of measuring device 25, the region of the so-called percolation threshold is provided as a control point, to which measured value 28 of measuring device 25 is to be controlled over the partial regeneration. The curve of measured value 28 of measuring device 25 plotted against the accumulation time per second, in the area of the percolation threshold shows an abrupt change, that is, in this area, a high gradient of the measured values 28 provides a sensitive measurement. After the exceeding of the percolation threshold, an additional accumulation of particles brings about only a small change in measured value 28.

In the case of the simultaneous operation of the discharge device for the DBE and the resistive measurement by interdigital comb electrodes 35, one should take care that DBE plasma 30 does not interfere with, or corrupt the resistive measurement. One suitable measure is a decoupling of the frequency ranges of the two devices using a lock-in technology. For example, one might choose the kHz range for the discharge generation and the 100 Hz range for the resistive measurement.

There is further the possibility of separating in time the partial regeneration and the resistive measurement, and, in this way, of avoiding cross influences or interferences. The two phases in time of the partial regeneration and the resistive measurement may alternate so rapidly that an almost continuous measurement is achieved. One may also carry out a cyclical operation mode using fixedly set phases of the partial regeneration and the resistive measurement.

Especially in the case of using DBE plasma 30, in response to a constant combustion period, the closing frequency of DBE plasma 30 may be varied, so that the regeneration performance of the accumulated particles adapts to the respective time unit. In a reverse manner, the possibility is also available of leaving the closing frequency of DBE plasma 30 constant, and of modulating instead the pulse width or the combustion period of DBE plasma 30. Finally, both the closing frequency and the combustion period of DBE plasma 30 may remain constant, and the performance of DBE plasma 30 may be modulated directly, for instance, via the voltages applied to discharge electrodes 35.

In a second exemplary embodiment as in FIG. 2, particulate sensor 5 has two base elements 40a, 40b. In the first, 40a, of the two base elements 40a, 40b, both an integrated heating element 45 and a control unit 20 having contact areas 21 are provided. Deviating from this, control unit 20 may be situated again in a control unit 23, which is electrically connected to sensor 5. The electrical connection is not shown in FIGS. 1 and 2, for reasons of clarity. Sensor 5 and control unit 23 together form a particle sensor system.

On the upper side, that is, on the side of second base element 40b facing first base element 40a of the two base elements 40a, 40b, interdigital comb electrodes 50 have been affixed which, again, are electrically connected to control unit 20 via contact areas 22. Heating element 45 and interdigital comb electrodes 50 are situated, in this context, in such a way that interdigital comb electrodes 50 are spatially situated downstream from heating element 45, in the exhaust gas flow direction.

As shown in FIG. 2 by the arrow direction, gas stream 55 having the particles to be detected, flows first through heating region 60. Heating region 60 is the spatial region that is able to be heated by heating element 45. After that, gas stream 55 arrives at measuring region 10, at which interdigital comb electrodes 50 have been applied. The particles present in gas stream 55 accumulate at measuring region 55. The particles adhering to measuring region 10 are measured by interdigital comb electrodes 50.

If it is determined, via a measurement of the conductivity change or the impedance change of measuring region 55 by interdigital comb electrodes 50 that the accumulation of the particles at measuring region 10 has advanced so far that the measured value 28 of interdigital comb electrodes 50 is in the range of the percolation threshold, heating element 45 is then activated. Within a short period, heater region 60 is heated to temperatures above the oxidation temperature of the particles. In this context, the combustion of the particles located in gas stream 55 is controlled by heating element 45 in such a way that exactly all the particles in gas stream 55 oxidize, and in measuring region 10 no further adhesion of particles takes place. In this specific embodiment, what is controlled is the heating performance, the voltage strength or the current strength of heating element 45.

The few particles which still flow through before reaching the oxidation temperature of heater region 60, and shortly thereafter become adhered in measuring region 10, do not, or only seldom, require a total regeneration of particle sensor 5. Thereby the signal/noise ratio is increased, and the accuracy of measured values 28 is increased.

Naturally, instead of using a heating element 45, a DBE plasma 30 may also find application here. In this context, DBE plasma 30 may be developed especially in the form of a curtain around measuring region 10 having measuring device 25, so as not to be dependent upon a directed exhaust gas flow.

What is claimed is:

1. A method for at least approximately continuously measuring particles in a gas stream in a measuring region of a particle sensor, the method comprising:
    accumulating the particles to be detected in the measuring region of the particle sensor;
    at least one of burning the accumulated particles by a partial regeneration of the measuring region, and burning the particles still located in the gas stream by a combustion device; and
    controlling combustion of the particles by the combustion device via a control signal from a control unit, which is connected to a measuring device, so that a quantity of the particles adhering in the measuring region remains constant, wherein the particles are removed via the partial regeneration to maintain the constant quantity of particles, determining from this, a signal amplitude of the particle sensor and correlating the signal amplitude to the quantity of particles in the gas stream.

2. The method of claim 1, wherein the combustion of the particles is performed when the particle sensor is in a range of a percolation threshold.

3. The method of claim 1, wherein a physical variable of the combustion device, which leads to the controlled combustion of the particles, is drawn upon as the signal amplitude of the particle sensor.

4. The method of claim 1, wherein the combustion of the particles and the measurement by the measuring device are performed alternatingly, especially cyclically.

5. The method of claim 1, wherein the particles include soot particles.

6. The method of claim 1, wherein the combustion of the particles and the measurement by the measuring device are performed cyclically.

7. The method of claim 1, wherein the combustion is performed by one of a dielectrically hindered discharge (DBE) and a heat intervention of the combustion device.

8. The method of claim 7, wherein a generation and operation of the DBE plasma and a measurement by the measuring device are performed at frequency ranges that are different from each other.

9. The method of claim 7, wherein the performance of the DBE plasma is made to correspond to the control signal by one of a varying closing frequency, a combustion period and a voltage supply.

* * * * *